United States Patent
Sauer et al.

(10) Patent No.: US 7,262,007 B2
(45) Date of Patent: Aug. 28, 2007

(54) DYE-LABELED OLIGONUCLEOTIDE FOR LABELING A NUCLEIC ACID MOLECULE

(75) Inventors: Markus Sauer, Heidelberg (DE); Jürgen Wolfrum, Rosdorf-Obernjesa (DE)

(73) Assignee: Markus Sauer, Heidelberg (DE)

( * ) Notice: Subject to any disclaimer, the term of this patent is extended or adjusted under 35 U.S.C. 154(b) by 400 days.

(21) Appl. No.: 10/146,255

(22) Filed: May 15, 2002

(65) Prior Publication Data
US 2003/0003486 A1    Jan. 2, 2003

Related U.S. Application Data

(63) Continuation of application No. PCT/DE99/03635, filed on Nov. 16, 1999.

(51) Int. Cl.
| | |
|---|---|
| C12Q 1/68 | (2006.01) |
| C12P 19/34 | (2006.01) |
| C07H 21/04 | (2006.01) |
| C07H 21/02 | (2006.01) |

(52) U.S. Cl. ..................... 435/6; 435/91.1; 536/22.1
(58) Field of Classification Search ............... 536/24.3; 435/6
See application file for complete search history.

(56) References Cited

U.S. PATENT DOCUMENTS 5,525,711 A    6/1996    Hawkins et al. ........... 536/22.1

FOREIGN PATENT DOCUMENTS

| WO | 0 745 690 A2 | 12/1996 |
|---|---|---|
| WO | WO98 02 449 A1 | 1/1998 |
| WO | WO98/10096 | 3/1998 |
| WO | WO98/26093 A2 | 6/1998 |

OTHER PUBLICATIONS

Sauer et al.: "New Fluorescent Dyes in the Red . . . ", Journal of Fluorescence, vol. 5, No. 3, 1995, p. 247-261.
Kostrikis et al.: "Spwectral Genotyping of Human Alleles", in: Science, vol. 279, p. 1228-1229.
Tyagi et al.: "Molecular Beacons: Probes that Fluoresce upon Hybridization", in Nature Biotechnology, vol. 14, Mar. 1996, p. 303308.
Seidel et a.: "Nucleobase-Specific Quenching of Fluorescent Dyes . . . . ", in: Journal of Physical Chemistry, vol. 100, p. 5541-5553.
Sauer et al.: "Dynamics of the Electron transfer reaction between an oxazine dye and DNA . . . ", in: Chemican Physics Letters, vol. 284, p. 153-63.
Chemical Abstracts, vol. 130, Ref. 262688, 1999.
Chemical Abstracts, vol. 130, Ref. 247503, 1999.
Chemical Abstracts, vol. 130, Ref. 11085k, 1999.
Chemical Abstracts, vol. 129, Ref. 286496v, 1998.
Chemical Abstracts, vol. 129, Ref. 23799p, 1998.
Chemical Abstracts, vol. 128, Ref. 85094t, 1998.
Chemical Abstracts, vol. 128, Ref. 163303b, 1998.
Chemical Abstracts, vol. 126, Ref. 259686p, 1997.
Chemical Abstracts, vol. 122, Ref. 3220v, 1995.
Chemical Abstracts, vol. 121, Ref. 225476b, 1994.
Chemical Abstracts, vol. 96, Ref. 63552j, 1982.
Chemical Abstracts, vol. 124, Ref. 251968v, 1996.
Molecular Beacons: A Novel DNA Probe for Nucleic Acid and Protein Studies, Weihong Tan et al., Chem. Eur. J. 2000, 6, No. 7, Wiley-VCH Verlag GmbH, pp. 1107-1111.
Molecular Beacons: A Real-Time Polymerase Chain Reaction Assay for Detecting Salmonella, Wilfried Chen et al., Analytical Biochemistry 280, 2000, pp. 166-172.
Molecular Beacon-Based Homogeneous Fluorescence PCR Assay for the Diagnosis of Infectious Diseases, Qing-Ge Li et al., Analytical Sciences, Feb. 2000, vol. 16, pp. 245-248.
Wavelength-shifting molecular beacons, Sanjay Tyagi et al., Nature Biotechnolgy, vol. 18, Nov. 2000, pp. 1191-1196.
Chemical Abstract AN 119:258762 [Photochemistry and Photobiology (1993), 58, (2), 185-94] ISSN: 0031-8655, "Mechanism of quenching of the fluorescence of a benzo[a]pyrene tetraol metabolite model compound by 2'-deoxynucleosides".

*Primary Examiner*—James Martinell
(74) *Attorney, Agent, or Firm*—Henry M. Feiereisen; Ursula B. Day

(57) ABSTRACT

The invention relates to an oligonucleotide which serves as a nucleic acid probe comprising a loop section with a loop sequence complementary to the target sequence of the nucleic acid molecule; a stem section arranged on both ends of the loop section for hybridizing with each other for closing the oligonucleotides thereby forming a loop, and wherein one of the stem sections is labeled with fluorescent color, such that when the loop section hybridizes with the target sequence of the nucleic acid, the oligonucleotide opens and the distance between the fluorophore and a quencher nuleoside increases which thereby prevents quenching of the fluorescence and the strength of fluorescence when measured indicates the presence of the nucleic acid with the target sequence.

16 Claims, 4 Drawing Sheets

Fig. 5
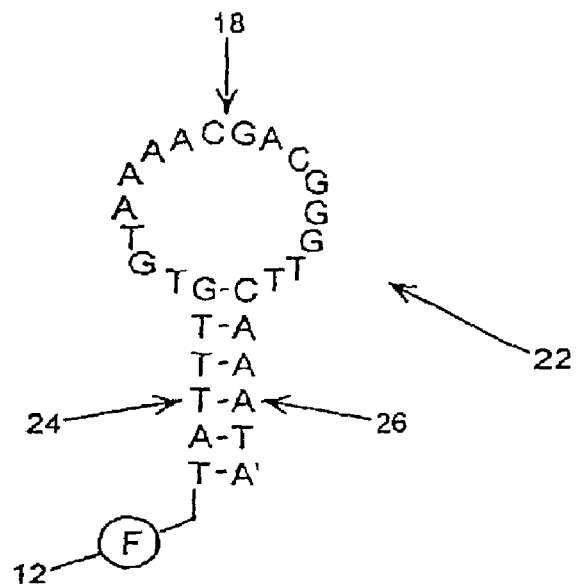
Fig. 6

DYE-LABELED OLIGONUCLEOTIDE FOR LABELING A NUCLEIC ACID MOLECULE

CROSS-REFERENCES TO RELATED APPLICATIONS

This application is a continuation of prior filed copending PCT International application no. PCT/DE99/03635, filed Nov. 16, 1999.

BACKGROUND OF THE INVENTION

The invention relates to a dye-labeled oligonucleotide for labeling a nucleic acid molecule having a target sequence section, the dye-labeled oligonucleotide having the following components: a loop section which has a loop sequence essentially complementary to said target sequence; a first stem section having at least three nucleosides and arranged at one end of the loop section; a second stem section having at least three nucleosides and arranged at the other end of the loop section, the two stem sections being able to hybridize intramolecularly; and a fluorophore which is bound to a position of the first stem section.

The invention further relates to the use of the dye-labeled oligonucleotide for labeling in a solution a nucleic acid molecule having a target sequence section and for two methods for detecting in a solution a nucleic acid molecule having a target sequence section.

The dye-labeled oligonucleotides mentioned at the outset are frequently called "nucleic acid probes". They play a central part in the rapid and sensitive detection of specific known nucleic acid molecules (DNA or RNA) in biological samples in molecular biology and biotechnology. Specific applications include, inter alia, medical early recognition of a bacterial or viral infection, forensics, use in DNA/RNA amplification by PCR or by other techniques, in the early diagnosis of a genetic defect and in discriminating between similar organisms and alleles.

A variety of methods for detecting nucleic acids and determining the amount of nucleic acids are known. The ubiquitous Southern blotting method is characterized by time-consuming steps and poor sensitivity.

A relatively new elegant method for detecting a specific nucleic acid molecule uses "molecular beacons" (Tyagi et al. 1996, Nature Biotechnology 14, 303–308; Kostrikis et al. 1998, Science 279, 1228–1229). Molecular beacons are dye-labeled oligonucleotides which have the stem-loop structure mentioned at the beginning. A fluorophore is coupled to each of the two free ends of the stem sections (3' and 5' ends). One fluorophore serves as fluorescent dye and the other one as quenching dye, which quenches the fluorescence of the fluorescent dye via Foerster energy transfer when in sufficiently close spatial proximity.

The sequences of the stem sections on both ends of the molecular beacons are chosen such that, when the molecular beacon folds, the stem sections hybridize exclusively with one another but not with other sections of the oligonucleotide. In the state of hybridized stem sections, the distance between the fluorescent dye and the quenching dye is sufficiently short so that the fluorescent dye does not fluoresce, even with suitable excitation with light.

The loop section has a sequence, which is complementary to the sequence of the target sequence section. If the molecular beacons and the DNA/RNA molecules having the target sequence are in a solution together, it is possible for the loop sections and the target sequence sections to hybridize. The sequences and lengths of the stem sections and loop sections are chosen such that the molecular beacon unfolds with breaking-up of the hybridization of the two stem sections. Due to said unfolding, the spatial distance between the fluorescent dye and the quenching dye is greatly increased. The fluorescent dye can then be excited to emit fluorescence.

If the fluorescence intensity of the fluorescent dye is observed continuously, an increase can be detected when the molecular beacons detect the target sequence sections of the nucleic acid molecules and hybridize therewith. In this way it is possible to detect the nucleic acid molecules quantitatively.

The disadvantage of this type of molecular beacons is their relatively complicated synthesis, since the oligonucleotide must be labeled specifically with the fluorescent and the quenching dye both on the 5' and on the 3' end.

It would therefore be desirable and advantageous to provide an improved dye-labeled oligonucleotide to obviate prior art shortcomings and to provide a suitable dye-labeled oligonucleotide for detecting nucleic acids in solution.

SUMMARY OF THE INVENTION

According to one aspect of the present invention, an improved detection of a nucleic acid molecule with the aid of a dye-labeled oligonucleotide is provided.

According to the invention, this aspect is exemplified by a dye-labeled oligonucleotide wherein a dye-labeled oligonucleotide for labeling a nucleic acid molecule having a target sequence section, the oligonucleotide comprises:

a loop section having a loop sequence essentially complementary to the target sequence; a first stem section having at least three nucleosides and arranged at one end of the loop section; a second stem section having at least three nucleosides and arranged at another end of the loop section, with the first and second stem sections capable of hybridizing with one another; and a fluorophore, which is bound to a position of the first stem section; wherein the second stem section has at least one quencher nucleoside; and wherein the sequence of the first and second stem section, the sequence of the loop section, the position of the fluorophore, the quencher nucleoside and the fluorophore are suited to one another such that in a hybridized state of the two stem sections, the fluorophore and the quencher nucleoside are spatially sufficiently close such that no fluorescence quenching of the fluorophore can take place during hybridization of the loop section with the target sequence section and breakup of the hybridization of the stem sections.

In another aspect of the invention, a method is provided for detecting in a solution a nucleic acid molecule having a target sequence section, comprising the steps of hybridizing a dye-labeled oligonucleotide of the afore-described type with a nucleic acid molecule and thereafter exciting the fluorophore to a fluorescence, detecting the fluorescence decay and recording the fluorescence decay in recordable form.

In yet another aspect of the invention, a method is provided for detecting in a solution a nucleic acid molecule having a target sequence section comprising the steps of hybridizing a dye-labeled oligonucleotide of the afore-described type with a nucleic acid molecule and thereafter adjusting the pH of said solution to values of between 2 and 4, and then recording a detection signal.

The present invention resolves prior art problems by the finding that the fluorescence of various fluorophores can be quenched by nucleosides via a photoinduced electron transfer (Sauer et al. 1995, J. Fluoresc. 5, 247–261; Seidel et al. 1996, J. Phys. Chem. 100, 5541–5553). The efficiency of fluorescence quenching by photoinduced electron transfer strongly depends on the distance between fluorophore and nucleoside, i.e. noticeable fluorescence quenching takes place only at a short distance between fluorophore and the suitable nucleoside (in a single or double strand). It was found that, for example, a guanosine which is more than 4 bases away from the coupling site of the fluorophore has no noticeable influence on the fluorescence ability of said fluorophore, as long as the fluorophore is bound to the corresponding nucleoside only via a very short spacer. This is true both for a guanosine in the same strand as the fluorophore and for those in the opposite strand.

In the dye-labeled oligonucleotide of the invention, the second stem section has at least one quencher nucleoside which quenches the fluorescence of the fluorophore by photoinduced electron transfer when in sufficient spatial proximity to said fluorophore. The sequence of the first stem section and the position of the fluorophore are chosen such that in the hybridized state of the two stem sections the fluorophore and the quencher nucleoside are spatially close enough for a fluorescence quenching and that no fluorescence quenching of the fluorophore takes place during hybridization of the loop section with the target sequence section and breaking-up of the hybridization of the stem sections.

A dye-labeled oligonucleotide of this kind (or a nucleic acid probe of this kind) has a number of advantages. Only a single fluorophore is needed, resulting in a simplified synthesis. Since the mechanism of fluorescence quenching by photoinduced electron transfer is well understood, it is also possible to specifically optimize fluorescence quenching.

Nucleoside and fluorophore must be suited to one another for efficient quenching. Of the naturally occurring nucleosides, guanosine is the most effective in quenching rhodamine dyes. The quenching efficiency can be increased by using 7-deazaguanosine as quencher nucleoside. In both cases it is possible that all other nucleosides of the second stem section are guanosines. Accordingly, cytidines can be chosen as nucleosides of the first stem section.

The sequence of the first stem section may be chosen such that the first stem section cannot hybridize with a section of the nucleic acid molecule, which is adjacent to the target sequence section. Otherwise, the fluorophore of the first stem section could get close to a guanosine acting as quencher.

Another quencher nucleoside which may be used is 7-deazaadenosine. Using 7-deazaadenosine as quencher drastically increases the quenching effect on the fluorophore in comparison with the unmodified guanosine. If 7-deazaadenosine is used as quencher nucleoside, the fluorophore is advantageously coupled to thymidine (in the case of DNA molecules) or uridine (in the case of RNA molecules). These nucleosides form base pairs with 7-deazaadenosine when the two stem sections hybridize.

If 7-deazaadenosine is used as quencher nucleoside on the second stem section and the fluorophore is coupled to thymidine or uridine, the fluorophore faces in the double strand a natural unmodified adenosine when the first stem section has hybridized with a section of the nucleic acid molecule. This leaves the fluorescence of the fluorophore essentially unaffected. Therefore, hybridization of the first stem section with a section of the nucleic acid molecule, which is adjacent to the target sequence section, can be allowed as long as the sequences of the first stem section and of the target sequence section are chosen such that no guanosine is close to the fluorophore. Hybridization of the first stem section to a section of the nucleic acid molecule places the fluorophore in a well-defined environment and, as a result, uncontrollable hybridizations with other nucleic acid molecules in the solution are avoided.

Guanosine, 7-deazaguanosine and 7-deazaadenosine may also be used mixed in the second stem section.

A particularly simple synthesis of the dye-labeled oligonucleotide may be obtained if the first stem section is arranged at the 5' end of the loop section and the fluorophore is coupled terminally to the terminal nucleoside.

Another advantageous possibility arises if the first stem section is arranged at the 3' end of the loop section, the fluorophore is coupled terminally to the terminal nucleoside of the first stem section and the 5' end of the second stem section is functionalized for immobilization. In this way it is possible to immobilize the nucleic acid probes, for example, on a DNA chip. The latter may indicate a hybridization via a fluorescent signal.

The 5' end of the second stem section may be functionalized with an acrylamide molecule. A nucleic acid probe functionalized in this way may be immobilized by copolymerization during preparation of a polyacrylamide gel. This may take place at a particular position in a slab gel or in a capillary. A sample to be studied which may contain nucleic acid molecules with very different sequences is then fractionated in the gel under nondenaturing conditions. The presence of a nucleic acid molecule having the target sequence section is indicated by a corresponding signal at the position of the immobilized nucleic acid probe in the gel. The nucleic acid molecule having the target sequence section may then be specifically isolated, for example by excision from the slab gel.

The loop section must be long enough so as to break up hybridization of the two stem sections when hybridization with the target sequence section takes place. On the other hand it must be only long enough for the target sequence section to be unambiguously identified. Therefore the loop section advantageously comprises 8 to 50 nucleosides.

The minimum length of the two stem sections must be such that reliable hybridization can take place. On the other hand, however, hybridization of the two stem sections should be broken up in the case of hybridization of the loop section with the target sequence section. The hybridization strength can be influenced via the length of the two stem sections. Advantageously, the first stem section therefore comprises 3 to 8 nucleosides and the second stem section at least as many nucleosides as the first stem section.

Suitable fluorophores are in principle all known dye molecules, but especially rhodamine and phenoxazine dyes. The latter can be readily coupled and are photostable. Another advantage of using rhodamine or phenoxazine dyes is the fact that small and inexpensive diode lasers can be used as excitation light source for fluorescence detection.

The dye-labeled oligonucleotide of the invention may be used advantageously for labeling in a solution a nucleic acid molecule having a target sequence section, with the dye-labeled oligonucleotide hybridizing with the nucleic acid molecule.

Moreover, the dye-labeled oligonucleotide of the invention is particularly suitable for detecting in a solution a nucleic acid molecule having a target sequence section. For this purpose, the nucleic acid molecule is labeled with a dye-labeled oligonucleotide of the invention. The double strand of probe and nucleic acid molecule is stabilized and the quenching efficiency between quencher and fluorophore is improved by adjusting the pH of the solution to values of between 2 and 4 after hybridization and prior to recording a detection signal. In order to avoid that fluctuations in the intensity, owing to, for example, inhomogeneities of the solution, affect the measurement results, it is possible to excite and detect the fluorescence of the fluorophore such that the fluorescence decay behavior thereof is recorded.

Examples of advantageous developments of the present invention are characterized in the appended claims.

BRIEF DESCRIPTION OF THE DRAWING

Other features and advantages of the present invention is illustrated in more detail below on the basis of exemplary embodiments which are diagrammatically depicted in the figures. Identical reference numbers in the individual figures denote identical elements. In detail, the figures show in FIG. 1 a dye-labeled oligonucleotide in which the stem sections are hybridized to one another showing exemplary SEQ ID NO. 1;

FIG. 5 a third exemplary embodiment of a dye-labeled oligonucleotide, in which the stem sections are hybridized to one another showing exemplary SEQ ID NO. 7;

FIG. 6 the dye-labeled oligonucleotide SEQ ID NO. 2 in which the loop section is hybridized to a nucleic acid molecule showing exemplary SEQ ID NO. 9.

DETAILED DESCRIPTION OF PREFERRED EMBODIMENTS

Figure 1:
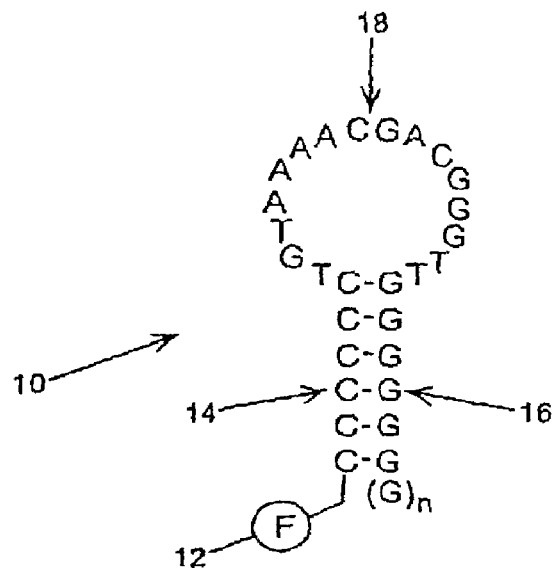

Throughout all the Figures, same or corresponding elements are generally indicated by same reference numerals.

In the figures the letters A, C, G and T denote the nucleosides adenosine, cytidine, guanosine and thymidine.

Photoinduced electron transfer is to be briefly illustrated below on the basis of FIG. 7 which depicts fluorescence quenching of an excited dye molecule F* by a nucleoside N. The black circles represent electrons. In each case, the HOMO (highest occupied molecular orbital) and the LUMO (lowest unoccupied molecular orbital) are drawn in. The HOMO is the occupied molecular orbital on the highest energy level in the electronic ground state. The LUMO is the unoccupied molecular orbital on the lowest energy level in the electronic ground state and is normally the molecular orbital which is occupied in the first excited state.

In principle there are two possibilities for fluorescence quenching by photoinduced electron transfer. In the case depicted in FIG. 7 left, the nucleoside N acts as electron donor. After excitation of the fluorophore F*, an electron is transferred from the doubly occupied HOMO of the nucleoside to the now singly occupied HOMO of fluorophore F* (1). As a result, the excited fluorophore F* is reduced by nucleoside N. The electron in the LUMO of the fluorophore can then be transferred to the now single-occupied HOMO of nucleoside N(2). This is the case in an interaction between guanosine and rhodamine molecules.

Figure 7:
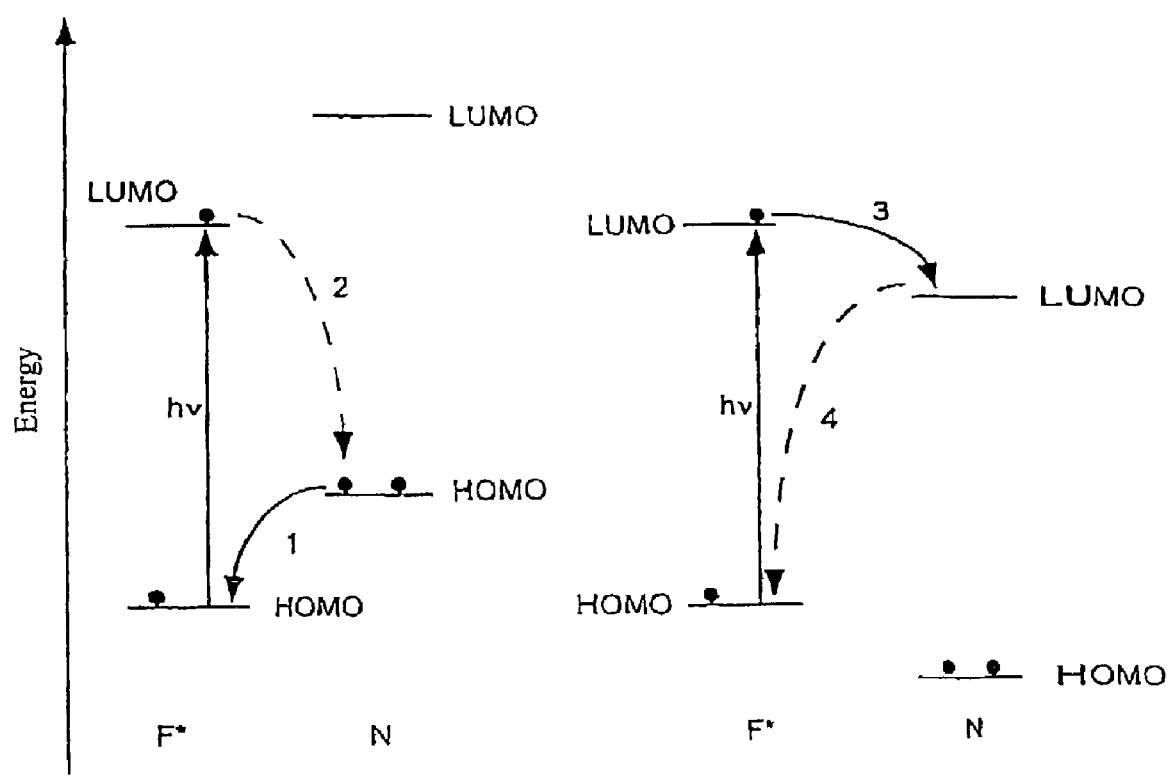
FIG. 7 a diagrammatic representation of the possible changes of state in photoinduced electron transfer.

In the case depicted in FIG. 7 right, the nucleoside N acts as electron acceptor. The electron present in the single-occupied LUMO of the excited fluorophore F* is transferred to the unoccupied LUMO of nucleoside N(3). As a result, the excited fluorophore F* is oxidized by nucleoside N. The electron in the LUMO of the nucleoside can then return to the HOMO of the fluorophore (4).

In both cases, it is, after the electron transfer, no longer possible for the electron to return from the LUMO of the excited fluorophore F* to the HOMO by emitting a photon. The first excited state was deactivated without radiative emission. The fluorescence has been quenched.

FIG. 1 depicts an oligonucleotide 10 to one end of which a fluorophore 12 is coupled. The oligonucleotide 10 consists of a first stem section 14, a second stem section 16 and a loop section 18. The sequence of the first stem section 14 consists of 6 nucleosides all of which are cytidines. The sequence of the second stem section 16 consists of at least 6 guanosines. This makes it possible for the first stem section 14 and the second stem section 16 to hybridize to one another and to fold the oligonucleotide 10 into a stem-loop structure. The precise length of the second stem section is unimportant as long as it has at least as many nucleosides as the first stem section.

Figure 2:
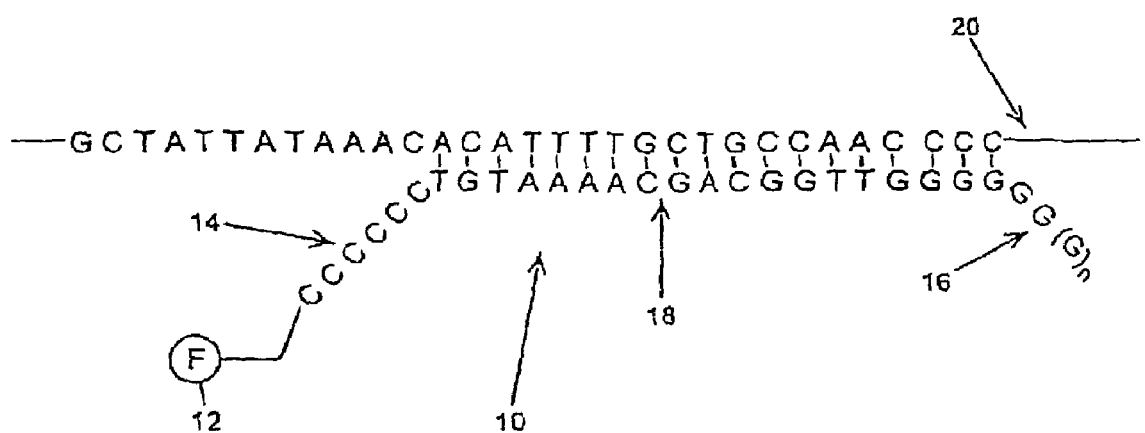
FIG. 2 the dye-labeled oligonucleotide SEQ ID NO. 3 (lower strand) in which the loop section is hybridized to a nucleic acid molecule showing exemplary SEQ ID NO. 8 (upper strand)

The following refers to FIG. 2. The sequence of the loop section 18 is chosen such that the oligonucleotide 10 can serve as a probe for a specific nucleic acid molecule 20. Normally, the loop sequence is complementary to the sequence of a target section of the nucleic acid molecule 20. If the oligonucleotide 10 and the nucleic acid molecule 20 are introduced into a solution together, the loop section 18 hybridizes to the target sequence section of the nucleic acid molecule 20. As a result, hybridization between the two stem sections 14, 16 is broken up. Consequently, the distance between the fluorophore 12 and the guanosines of the second stem section 16 increases. The latter no longer act as fluorescence quenchers on the fluorophore 12 whose fluorescence can thus be observed. An increase in the fluorescence of the fluorophore 12 therefore allows qualitative and quantitative statements about the presence of the nucleic acid molecule 20.

In this exemplary embodiment, the target sequence section on the nucleic acid molecule 20 is chosen in a way that the first stem section 14 does not hybridize with the nucleic acid molecule 20 during hybridization of the loop section 18. This avoids in principle the proximity to any guanosines on this section of the nucleic acid molecule 20. However, FIG. 2 indicates that the second stem section 16, for example, can partially hybridize to the nucleic acid molecule.

Figure 3:
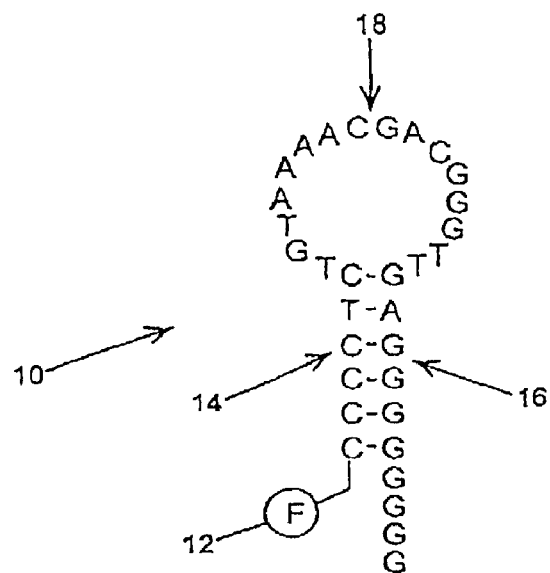
FIG. 3 a second exemplary embodiment of a dye-labeled oligonucleotide in which the stem sections are hybridized to one another showing exemplary SEQ ID NO. 4.

The following refers to FIG. 3. FIG. 3 shows a second exemplary embodiment of a dye-labeled oligonucleotide 10 which is essentially identical to the oligonucleotide according to FIG. 1. However, the oligonucleotide according to FIG. 3 has in the first stem section 14 a thymidine as a fifth nucleoside, counted from the end. The second stem section has an adenosine as a ninth nucleoside, again counted from the end. In the hybridized double strand, said adenosine and said thymidine form a base pair. It is then not possible for the cytidines and guanosines to hybridize in staggered positions toward one another. This ensures that, as a result, one end has a guanosine overhang which facilitates quenching of the fluorophore.

Figure 4:
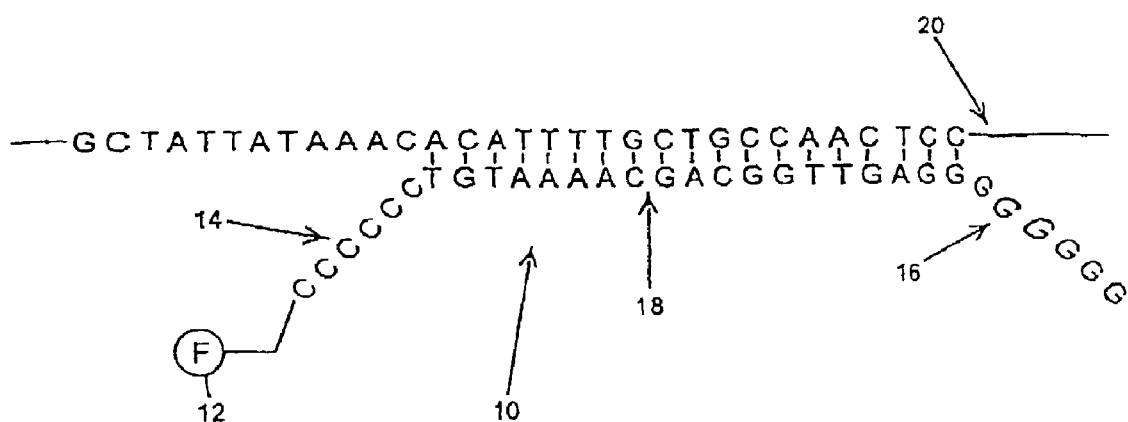
FIG. 4 the dye-labeled oligonucleotide SEQ ID NO. 6 in which the loop section is hybridized to a nucleic acid molecule showing exemplary SEQ ID NO. 5.

FIG. 4 shows the oligonucleotide 10 according to FIG. 3, hybridized to a nucleic acid molecule 20 which has a target sequence section whose sequence is complementary to the loop sequence.

The following refers to FIG. 5. FIG. 5 shows a second exemplary embodiment of a dye-labeled oligonucleotide 22 having a first stem section 24 and a second stem section 26. The second stem section 26 has exactly 6 nucleosides of which the terminal nucleoside is a modified adenosine, more accurately 7-deazaadenosine which is indicated by A' in FIGS. 5 and 6. Accordingly, the site of the first stem section 24, which is opposite to 7-deazaadenosine in the hybridized state of the two stem sections 24, 26, is occupied by a thymidine to which the fluorophore 12 is coupled.

FIG. 6 shows the nucleic acid molecule 20 according to FIG. 2, to which the dye-labeled oligonucleotide 22 according to FIG. 5, which serves as a probe, is hybridized. FIGS. 2 and 6 differ only in that the stem sections 14, 16 and 24, 26, respectively, have different sequences. In FIGS. 5 and 6, the first stem section 24 has a sequence which makes it possible for said first stem section 24 to hybridize with a section of the nucleic acid molecule 20, which is adjacent to the target sequence section.

a) The target sequence section and the corresponding sequence of the oligonucleotide 22 may be determined in the following way:

b) The nucleic acid molecule 20 is screened for an adenosine for which neither cytidine nor guanosine are among the in each case 4 nucleosides neighboring said adenosine to the left and right.

c) The extended neighborhood of said adenosine, for example at least 9 nucleosides in 5' direction of the nucleic acid molecule 20, is searched for a sequence which unambiguously characterizes the nucleic acid molecule 20.

d) The oligonucleotide sequence 22 is formed complementary to said sequence. In this connection, the first 3 to 6 nucleosides on the 5' end of the oligonucleotide sequence form the first stem sequence 24.

e) The second stem sequence 26 is obtained in the following way: it is checked whether the 3' end of the oligonucleotide sequence da) contains 3 to 6 nucleosides which are intramolecularly complementary exclusively to the first stem sequence, and whether db) the 3' terminal nucleoside is adenosine.

If this is the case, these 6 nucleosides form the second stem sequence 26.

If this is not the case, the oligonucleotide sequence is extended by 3 to 6 nucleosides such that the result is 3 to 6 nucleosides which are intramolecularly complementary exclusively to the first stem sequence and have a 3' terminal adenosine. (If this is not possible, for example because the sequence of the first stem section is repeated within the target sequence, a different adenosine must be searched for according to step a).)

In the synthesis of the oligonucleotide, 7-deazaadenosine replaces the 3' terminal adenosine.

(The minimum number of 9 nucleosides in step b) results from the minimum length of the oligonucleotide sequence consisting of 3 nucleosides for the two stem sequences 24, 26 and at least 4 nucleosides for the folding section of the oligonucleotide.)

This example shows that the loop and stem sections can also overlap and that the dye-labeled oligonucleotide 22 can also completely hybridize to the nucleic acid molecule 20.

(a) In principle, the dye may be coupled both to the 3' end and to the 5' end of the oligonucleotide. To this end, the following possibilities are available:

(b) Known modification of one end of the oligonucleotide with an amine function, for example by a C6-amino linker and subsequent coupling of the dye to the modified end via an activated carboxyl function.

(c) Synthetic incorporation of an amino-modified nucleotide during synthesis of the oligonucleotide, for example in a synthesizer, and subsequent coupling of the dye to the amino-modified nucleotide via an activated carboxyl function.

Synthetic incorporation of the dye as phosphoramidite during oligonucleotide synthesis.

To optimize the quenching efficiency, firstly the double strand formed by hybridization must be as stable as possible. This is achieved in the known manner by adjusting appropriate salt concentrations. Secondly, however, the pH can drastically influence the quenching efficiency, for example when using a rhodamine dye carrying a free carboxyl group, for example tetramethylrhodamine. Protonation of the free carboxyl function in acidic medium reduces repulsion between the dye and the phosphate groups of the nucleotides. The latter event leads to a shorter distance between dye and nucleotides or nucleosides and thus to stronger fluorescence quenching. When using appropriate dyes, the pH is therefore adjusted to approx. pH 3 prior to recording a detection signal.

The nucleic acid molecule is detected by detecting the fluorescence of the fluorophore, preferably using time-correlated single photon counting (D.V. O'Connor and D. Phillips; "Time-correlated single photon counting", Academic Press, London, 1984). Apart from the particularly high sensitivity, this spectroscopic technique has the advantage that with the aid thereof it is possible to observe the fluorescence decay behavior of the fluorophore 12. This has proved to be a more reliable criterion for detecting the fluorescence of the fluorophore 12 and thus of the nucleic acid molecule 20 than simple intensity measurement. Intensity fluctuations, owing to, for example, inhomogeneities in the solution, therefore have no effect on the measurement results.

Within the scope of the present invention, numerous modifications and developments of the exemplary embodiments described can be realized. Thus, for example, the fluorophore 12 need not be coupled directly to the particular nucleoside which is opposite the quencher nucleoside in the hybridized state. The distance to the first-mentioned nucleoside only needs to be small enough to cause useful fluorescence quenching by the quencher nucleoside. Likewise, the loop section 18 and the stem sections 14, 16, 24, 26 need not be adjacent to one another but may be separated from one another by other short sequence sections. The sequence of the target section and thus the complementary sequence of the loop section 18 can in principle be any sequence. Moreover, the nucleic acid molecule 20 may consist exclusively of the target sequence section.

While the invention has been illustrated and described as embodied in a dye-labeled oligonucleotide for detecting nucleic acids, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

SEQUENCE LISTING

<160> NUMBER OF SEQ ID NOS: 9

<210> SEQ ID NO 1
<211> LENGTH: 28
<212> TYPE: DNA
<213> ORGANISM: Artificial
<220> FEATURE:
<223> OTHER INFORMATION: this sequence is exemplary to show a
      dye-labelled ologonucloetide in which the stem portions are
      hybridized to one another

<400> SEQUENCE: 1 cccccctgt aaacgacgg gttggggggg                                   28

<210> SEQ ID NO 2
<211> LENGTH: 31
<212> TYPE: DNA
<213> ORGANISM: Artificial
<220> FEATURE:
<223> OTHER INFORMATION: This sequence is exemplary to show dye-labeling
      when portions thereof are hybridized with a nucleic acid

<400> SEQUENCE: 2
gctattataa acacattttgc tgccaacccc                                31

<210> SEQ ID NO 3
<211> LENGTH: 27
<212> TYPE: DNA
<213> ORGANISM: Artificial
<220> FEATURE:
<223> OTHER INFORMATION: a dye-labelled oligonucleotide in which the
      loop section id hybridized to a nucleic acid molecule

<400> SEQUENCE: 3 ccccctgta aacgacggt tggggg                                       27

<210> SEQ ID NO 4
<211> LENGTH: 32
<212> TYPE: DNA
<213> ORGANISM: Artificial
<220> FEATURE:
<223> OTHER INFORMATION: this sequence is exemplary for a dye-labelled
      oligo nucleotide in which the stem portions are hybridized to one
      another

<400> SEQUENCE: 4 ccctctgta aacgacggg ttgagggggg gg                                32

<210> SEQ ID NO 5
<211> LENGTH: 31
<212> TYPE: DNA
<213> ORGANISM: Artificial
<220> FEATURE:
<223> OTHER INFORMATION: this sequence is exemplary for a dye-labelled
      oligonucleotide in which the loop portion is hybridized to a
      nucleic acid molecule

<400> SEQUENCE: 5
gctattataa acacattttgc tgccaactcc                                31

<210> SEQ ID NO 6
<211> LENGTH: 31
<212> TYPE: DNA
<213> ORGANISM: Artificial
<220> FEATURE:
<223> OTHER INFORMATION: a dye-labelled oligonucleotide in which the -continued

```
        loop section is hybridized to a nucleic acid molecule

<400> SEQUENCE: 6
cccccctgta aaacgacggt tgagggggg g                                31

<210> SEQ ID NO 7
<211> LENGTH: 28
<212> TYPE: DNA
<213> ORGANISM: Artificial
<220> FEATURE:
<223> OTHER INFORMATION: this sequence is exemplary for a dye-labelled
      ologonucleotide in which the stem portions are hybridized to one
      another

<400> SEQUENCE: 7
tatttgtgta aaacgacggg ttcaaata                                   28

<210> SEQ ID NO 8
<211> LENGTH: 31
<212> TYPE: DNA
<213> ORGANISM: Artificial
<220> FEATURE:
<223> OTHER INFORMATION: this sequence is a exemplary for demonstrating
      dye labeling of hybridized portions thereof

<400> SEQUENCE: 8
gctattataa acacattttg ctgccaaccc c                               31

<210> SEQ ID NO 9
<211> LENGTH: 27
<212> TYPE: DNA
<213> ORGANISM: Artificial
<220> FEATURE:
<223> OTHER INFORMATION: a dye-labelled oligonucleotide in which the
      stem sections are hybridized to one another

<400> SEQUENCE: 9
tatttgtgta aaacgacggt tcaaata                                    27
```

What is claimed is:

1. A dye-labeled oligonucleotide for labeling a nucleic acid molecule having a target sequence section, the oligonucleotide comprising:
   a) a loop section having a loop sequence substantially complementary to the target sequence;
   b) a first stem section having at least three nucleosides and arranged at one end of the loop section;
   c) a second stem section having at least three nucleosides and arranged at another end of the loop section, with the first and second stem sections substantially complementary for hybridizing with one another; and
   d) a fluorophore, which is bound to a position of the first stem section;
   wherein the second stem section has at least one quencher nucleoside selected from the group consisting of guanosine, 7-deazaguanosine and 7-deazaadenosine;
   wherein the quencher nucleoside is not more than four bases away from a coupling site of the fluorophore with the fluorophore linked to the first stem section by a suitable spacer; and wherein the sequence of the first and second stem section and the sequence of the loop section, as well as the position and type of fluorophore are suitably selected relative to one other, such that in a hybridized state of the two stem sections, the fluorophore and the quencher nucleoside can interact for fluorescence quenching, and that no fluorescence quenching of the fluorophore can take place during hybridization of the loop section with the target sequence section and break-up of the hybridized stem sections.

2. The dye-labeled oligonucleotide of claim 1, wherein the first stem section is chosen such that when the loop section is hybridized with the target sequence section of the nucleic acid molecule, the first stem section, is also hybridized with a section of said nucleic acid molecule.

3. The dye-labeled oligonucleotide of claim 1, wherein the first stem section is arranged at a 5' end of the loop section; and the fluorophore is coupled terminally to a terminal nucleoside of said first stem section.

4. The dye-labeled oligonucleotide of claim 1, wherein the first stem section is arranged at a 3' end of the loop section; the fluorophore is coupled terminally to a terminal nucleoside of said first stem section; and a 5' end of the second stem section is operative for an immobilization.

5. The dye-labeled oligonucleotide of claim 4, wherein an acrylamide molecule is bound to the 5' end of the second stem section.

6. The dye-labeled oligonucleotide of claim 1, wherein the loop section comprises 8 to 50 nucleosides.

7. The dye-labeled oligonucleotide of claim 1, wherein the first stem section comprises not more than 8 nucleosides.

8. The dye-labeled oligonucleotide as claimed in claim 1, wherein the fluorophore has a rhodamine or phenoxazine dye molecule.

9. A method for detecting in a solution a nucleic acid molecule having a target sequence section, comprising the steps of hybridizing a dye-labeled oligonucleotide with a nucleic acid molecule, the oligonucleotide comprising:
   a) a loop section having a loop sequence substantially complementary to the target sequence;
   b) a first stem section having at least three nucleosides and arranged at one end of the loop section;
   c) a second stem section having at least three nucleosides and arranged at another end of the loop section, with the first and second stem sections capable of hybridizing with one another; and
   d) a fluorophore, which is bound to a position of the first stem section;
      wherein the second stem section has at least one quencher nucleoside selected from the group consisting of guanosine, 7-deazaguanosine and 7-deazaadenosine; and wherein the sequence of the first and second stem section, the sequence of the loop section, the position of the fluorophore being chosen and the quencher nucleoside and the fluorophore are suited to one another such that in a hybridized state of the two stem sections, the fluorophore and the quencher nucleoside are spatially sufficiently close for a fluorescence quenching, and that no fluorescence quenching of the fluorophore can take place during hybridization of the loop section with the target sequence section and break-up of the hybridization of the stem sections; and thereafter adjusting the pH of said solution to values of between 2 and 4, and then recording a detection signal.

10. A method for detecting in a solution a nucleic acid molecule having a target sequence section, comprising the steps of hybridizing a dye-labeled oligonucleotide with a nucleic acid molecule, the oligonucleotide comprising:
   a) a loop section having a loop sequence substantially complementary to the target sequence;
   b) a first stem section having at least three nucleosides and arranged at one end of the loop section;
   c) a second stem section having at least three nucleosides and arranged at another end of the loop section, with the first and second stem sections capable of hybridizing with one another; and
   d) a fluorophore, which is bound to a position of the first stem section;
      wherein the second stem section has at least one quencher nucleoside selected from the group consisting of guanosine, 7-deazaguanosine and 7-deazaadenosine; and wherein the sequence of the first and second stem section, the sequence of the loop section, the position of the fluorophore being chosen and, the quencher nucleoside and the fluorophore are suited to one another such that in a hybridized state of the two stem sections, the fluorophore and the quencher nucleoside are spatially sufficiently close for a fluorescence quenching, and that no fluorescence quenching of the fluorophore can take place during hybridization of the loop section with the target sequence section and break-up of the hybridized stem sections; and thereafter exciting the fluorophore to a fluorescence, detecting the fluorescence decay and recording the fluorescence decay in recordable form.

11. A method for producing a dye-labeled oligonucleotide for labeling a nucleic acid molecule having a target sequence section,
   (a) selecting a suitable loop section for the oligonucleotide, the oligonucleotide having a first and second stem section, each of the stem sections including at least three nucleosides;
   (b) selecting a quencher nucleoside and a fluorophore such that the quencher nucleoside quenches the fluorescence of the fluorophore when in sufficient spatial proximity to said fluorophore;
   (c) selecting the sequence of the loop and stem sections and a position of the fluorophore such that
      (i) the loop section can hybridize to the target sequence section of the nucleic acid molecule;
      (ii) the two stem section can hybridize with one another;
      (iii) in a hybridized state of the two stem sections a sufficient spatial proximity is given for fluorescence quenching between the fluorophore and the quencher nucleoside; and such that
      (iv) during hybridization of the loop section with the target sequence section and breaking up of the hybridization of the stem sections no fluorescence quenching of the fluorophore takes place;
   (d) synthesizing the oligonucleotide with the pre-determined sequence, whereby the fluorophore is bound to the first stem section and the quencher nucleoside is part of the second stem section.

12. A method for detecting in a solution a nucleic acid molecule having a target sequence section with a dye labeled oligonucleotide, comprising the steps of:
   (a) selecting an oligonucleotide having a suitable loop section, the oligonucleotide having a first and second stem section, each of the stem sections including at least three nucleosides;
   (b) selecting a quencher nucleoside and a fluorophore such that the quencher nucleoside quenches the fluorescence of the fluorophore when in sufficient spatial proximity to said fluorophore;
   (c) selecting the sequence of the loop and stem sections and a position of the fluorophore such that
      (i) the loop section can hybridize to the target sequence section of the nucleic acid molecule;
      (ii) the two stem section can hybridize with one another;
      (iii) in a hybridized state of the two stem sections a sufficient spatial proximity is given for fluorescence quenching between the fluorophore and the quencher nucleoside such that
      (iv) during hybridization of the loop section with the target sequence section and breaking up of the hybridization of the stem sections no fluorescence quenching of the fluorophore takes place;
   (d) synthesizing the oligonucleotide with the pre-determined sequence, whereby the fluorophore is bound to the first stem section and the quencher nucleoside is part of the second stem section; and
   (e) hybridizing the so synthesized dye-labeled oligonucleotide probe with the target sequence.

13. The method as claimed in claim 12, wherein at least one quencher nucleoside is guanosine or 7-deazaguanosine or 7-deazaadenosine.

14. The method of claim 12, wherein the first stem section is selected such that when the loop section hybridizes with the target sequence of the nucleic acid molecule, the first stem section can hybridize with a section of the nuclei acid molecule.

15. The method of claim 14, wherein an extension of the target sequence in a direction of where the first stem is present cannot include a quencher nucleoside.

16. The method of claim 12, wherein the first stem cannot include a quencher nucleoside.

* * * * *